(12) United States Patent
Oettinger et al.

(10) Patent No.: US 8,092,457 B2
(45) Date of Patent: Jan. 10, 2012

(54) DRILLING DEVICE AND DRILLING PROCEDURES FOR SURGICAL PURPOSES

(75) Inventors: Wolfgang Oettinger, Korlingen (DE); Wolfgang J. Parak, Dachau (DE)

(73) Assignee: Wolfgang Oettinger, Korlingen (DE)

( * ) Notice: Subject to any disclaimer, the term of this patent is extended or adjusted under 35 U.S.C. 154(b) by 1240 days.

(21) Appl. No.: 10/543,992

(22) PCT Filed: Jan. 30, 2004

(86) PCT No.: PCT/EP2004/000886
§ 371 (c)(1), (2), (4) Date: Apr. 17, 2006

(87) PCT Pub. No.: WO2004/066850
PCT Pub. Date: Aug. 12, 2004

(65) Prior Publication Data
US 2006/0241628 A1 Oct. 26, 2006

(30) Foreign Application Priority Data
Jan. 31, 2003 (DE) .................................. 103 03 964

(51) Int. Cl.
*A61B 17/00* (2006.01)
(52) U.S. Cl. ............. 606/80; 606/79; 606/104; 600/547
(58) Field of Classification Search ............. 606/79–81, 606/86 R, 914–916, 96–98, 104, 86 A, 86 B; 600/547, 550; 408/9, 14–16, 6–8, 12; 433/102, 433/224
See application file for complete search history.

(56) References Cited

U.S. PATENT DOCUMENTS

| | | | |
|---|---|---|---|
| 2,763,935 A | 9/1956 | Andrews et al. | |
| 4,111,208 A * | 9/1978 | Leuenberger | 606/80 |
| 4,243,388 A * | 1/1981 | Arai | 433/27 |
| 5,271,413 A * | 12/1993 | Dalamagas et al. | 600/547 |
| 5,411,503 A * | 5/1995 | Hollstien et al. | 606/86 R |
| 5,421,727 A * | 6/1995 | Stevens et al. | 433/224 |
| 5,474,558 A * | 12/1995 | Neubardt | 606/79 |
| 5,785,522 A | 7/1998 | Holmen et al. | |
| 5,833,693 A * | 11/1998 | Abrahami | 606/96 |
| 5,951,482 A * | 9/1999 | Winston et al. | 600/476 |
| 6,290,437 B1* | 9/2001 | Mattheck et al. | 408/2 |
| 6,337,994 B1* | 1/2002 | Stoianovici et al. | 600/547 |
| 6,391,005 B1 | 5/2002 | Melton, Jr. et al. | |
| 6,481,939 B1* | 11/2002 | Gillespie et al. | 409/131 |

(Continued)

FOREIGN PATENT DOCUMENTS
DE 36 15 632 A1 11/1987
(Continued)

*Primary Examiner* — Eduardo C Robert
*Assistant Examiner* — Jan Christopher Merene
(74) *Attorney, Agent, or Firm* — D. Peter Hochberg; Sean F. Mellino; Daniel J. Smola

(57) ABSTRACT

A medical drilling device for drilling of human or animal tissue carries a drill (7) that is electrically contacted by a bore electrode (9) and a backing electrode (10). Both electrodes (9, 10) are charged by a resistance-measuring device (11) in a way, that electrical resistance of tissue (2, 3, 4), preferably impedance, as measured between the drill (7) and the backing electrode (10) becomes measurable. By means of a monitoring device (13), the surgeon is provides with information about the type of the respective tissue and the depth of drilling.

18 Claims, 4 Drawing Sheets

U.S. PATENT DOCUMENTS

| | | | |
|---|---|---|---|
| 6,520,773 B1 * | 2/2003 | Weber | 433/27 |
| 6,872,075 B2 * | 3/2005 | Regan | 433/102 |
| 6,997,883 B1 | 2/2006 | Hahn | |
| 7,096,555 B2 * | 8/2006 | Tourne et al. | 29/402.06 |
| 7,121,827 B2 * | 10/2006 | Lampert | 433/72 |
| 7,410,468 B2 * | 8/2008 | Freeman et al. | 600/583 |
| 7,580,743 B2 * | 8/2009 | Bourlion et al. | 600/547 |
| 2002/0161372 A1 * | 10/2002 | Bolger et al. | 606/80 |
| 2002/0188183 A1 | 12/2002 | Kusakabe et al. | |
| 2003/0018279 A1 * | 1/2003 | Rosenblatt | 600/547 |
| 2003/0088189 A1 * | 5/2003 | Tu et al. | 600/549 |
| 2003/0105410 A1 * | 6/2003 | Pearlman | 600/547 |
| 2004/0019291 A1 * | 1/2004 | Thacker | 600/547 |
| 2005/0119660 A1 * | 6/2005 | Bourlion et al. | 606/80 |
| 2005/0131415 A1 * | 6/2005 | Hearn et al. | 606/80 |
| 2008/0183173 A1 * | 7/2008 | Jozat | 606/80 |

FOREIGN PATENT DOCUMENTS

| | | |
|---|---|---|
| DE | 3719 911 A1 | 12/1988 |
| DE | 197 14 167 A1 | 10/1998 |
| DE | 199 54 005 | 6/2001 |
| DE | 102 21 787 A1 | 1/2003 |
| EP | 1269933 | 1/2003 |
| WO | WO 03/068076 A1 | 8/2003 |

* cited by examiner

DRILLING DEVICE AND DRILLING PROCEDURES FOR SURGICAL PURPOSES

CROSS-REFERENCE TO RELATED APPLICATIONS

This application is a National Stage application of International Application No. PCT/EP2004/000886, filed on Jan. 30, 2004, which claims priority of German application number 103 03 964.3, filed on Jan. 31, 2003.

BACKGROUND OF THE INVENTION

1. Field of the Invention

The invention deals with a surgical drilling device and subsequent drilling procedure aiming at drilling holes in live human or animal bones. The device is equipped with a drilling drive rotating a drilling tool that conducts electrical currency.

2. Description of the Prior Art

Orthopedic surgery and trauma care require bone drilling when repair of fractures is indicated. The holes resulting from drilling accept screws to hold implants such as plates, prostheses or to exert pressure between broken and subsequently reduced bone fragments. The screws inserted have to fit allowing a length range of no more than one millimeter. Conventional measuring of length is using a mechanical slide gauge, which is unhandy, time consuming and erratic, sometimes requiring repeated x-ray-control and corrections, yet even tissue injury in rare cases.

The bones in question usually are of two major structures: cortical bone, which for example is stress carrying entity in tube-shaped long bones, and spongious bone, which e.g. is accumulated in the vicinity of joint surfaces.

Passing with a drill through a tube-shaped bone perpendicular to the long axis means penetrating at first the cortical layer, followed by spongious bone and reaching out through the opposite cortical layer to touch soft tissue surrounding the bone. The opposite cortex is normally covered by soft tissue, whereas the at the starting point, the small area, where the drill is attached before drilling on the nearside cortex is being either surgically exposed or reached transcutaneously by palpation with the aid of a socket. This socket protects soft tissue from immediate contact with the drill and equally helps to guide the drill, to give it the direction of choice.

Alternative matters to determine the depth of the drilled hole are provided by ultrasound techniques or use of lasers. These methods refer to variable reflections from soft tissue, cortical and spongious bone. These methods, however, are technically demanding and need separate measuring—as with the slide gauge—by interrupting the drilling act.

When drilling through bones, at the end the surgeon has to take care of the adjacent soft tissue after penetration the opposite cortex, thus to prevent this tissue from being injured. To make sure that this does not happen, some surgeons interrupt the drilling act in order to palpate with the non-rotating drill whether or not the cortex is penetrated. It is the object of this invention to simplify this manoeuvre by sparing the surgeon this interruption and simultaneously indicating the depth of the bore hole. This technical ability is provided by the demand number one of this invention. Furthermore, the invention in question refers to a medical drilling device which is equipped with a bore electrode (incorporated in the drill), a backing electrode as well as a measuring device for electrical resistance connecting both electrodes. Thus, the bore electrode is directly connected with the current conducting drilling device, while the backing electrode is mounted at an opposite distance to the drilling device, e.g. on the skin of the patient.

With the aid of the resistance measuring device, the two electrodes are exposed to continuous or alternating electrical current. Subsequently, the electrical resistance between the bore electrode and the backing electrode can be measured and indicated on a monitoring screen.

SUMMARY OF THE INVENTION

In an advantageous model of the invention, the resistance measuring device (RMD) produces an alternating current and registers resistance by the dimension of impedance. With this arrangement, it is possible to measure the electrical resistance of the tissue between the drilling device and the backing electrode particularly clean, i.e. without being disturbed by electrical fields or other static loads.

The basis of these mechanisms lies in the knowledge, that human and animal tissue particularly the contrast between soft and bone tissue, are characterised by different impedance levels. This allows to literally locate the tip of the drill on its way through the tissue. It was demonstrated that the tip of the drill by penetrating the opposite cortex and touching soft tissue leads to a significant change of impedance. Seeing that as an electrical or digital signal, the surgeon can conclude, that the tip of the drill has just penetrated the opposite cortex. By this, he can avoid injuring soft tissue and simultaneously know about the length of the needed screw.

It is of particular advantage, that continuous resistance measurement is possible during the drilling procedure, thus interrupting the drilling process is not necessary any more. A figure of electrical resistance is also given by applying continuous current. However, it needs to be verified whether this figure is sufficient to differentiate the various tissue types. It can be imagined, that continuous current is easily disturbed and thus lacking reliable data.

A particularly advantageous model of the invention offers a monitoring technique that indicates optical and acoustical signals based on measured resistance and the change of respective figures. This enables the surgeon to locate his bore tip. The data can be provided by absolute digits or by means of relative differences. The data processing can be arranged in a way that an automatic switch-off is integrated or a signal indicating the particular tissue quality, where the tip of the drill is presently located.

The drilling device, as characterised by this invention, does not only allow to determine time of penetration, but also to monitor the surgeon's conduct in particularly difficult, 3-dimensional regions such as in pelvic surgery. The surgeon is being navigated through narrow spongious bone without risk of accidentally penetrating adjacent cortex.

It is particularly useful, when the drilling device is equipped with an electrically conducting drill that is covered by insulating material. Due to this insulation, electrical current runs through the core of the drill only allowing electrical contacts at two points: At the tip of the drill and in a ring-like area on the bore shaft. In the last mentioned ring-like area, a voltage generating continuous or alternating current can be applied. The resulting current is conducted without disturbances to the drill's tip. At the end, electrical resistance between the tip of the drill and the backing electrode depending on the tissue's specific impedance can be precisely measured.

It is mandatory, that the rest of the bore shaft, which is mounted to a drilling chuck, is also electrically insulated to avoid errors in resistance measurements induced by the drilling chuck or the drive mounted behind.

Further development of the invention includes a device which can measure the drilling depth, i.e. by measuring the drilling advancement. Provided that measuring starts at a time, when the drill hits the first cortical surface, a precise measurement of the drilling hole's depth is possible. It is planned to indicate the measured advancement on a monitoring device, that can be observed by the surgeon and the assisting nurse, who usually selects the appropriate screw length. The time, when the drill hits the first cortical surface, is registered by a sensor operated by the surgeon. So is the time, when the drill leaves the opposite cortex.

It is obvious, that all materials and devices have to be stable enough to undergo sterilisation at 130° centigrade.

In summary, this invention refers to a drilling device that enables the surgeon to measure the length of the drilling hole and subsequently the length of the needed implant (screw). Simultaneously, i.e. without interrupting the procedure, it is possible to continuously locate the drill's tip and thus navigate through difficult, 3-dimensional tissue components as well.

Subsequently, this invention is going to prevent from repeated trials of implant fixation in case of wrong measurements and for that will safe operating time as well as repeated X-Ray-controls, which render unnecessary by this invention.

The above mentioned and further advantages and characteristics of the invention will be explained by the following drawings and practical examples:

DETAILED DESCRIPTION OF THE INVENTION

Figure 1:
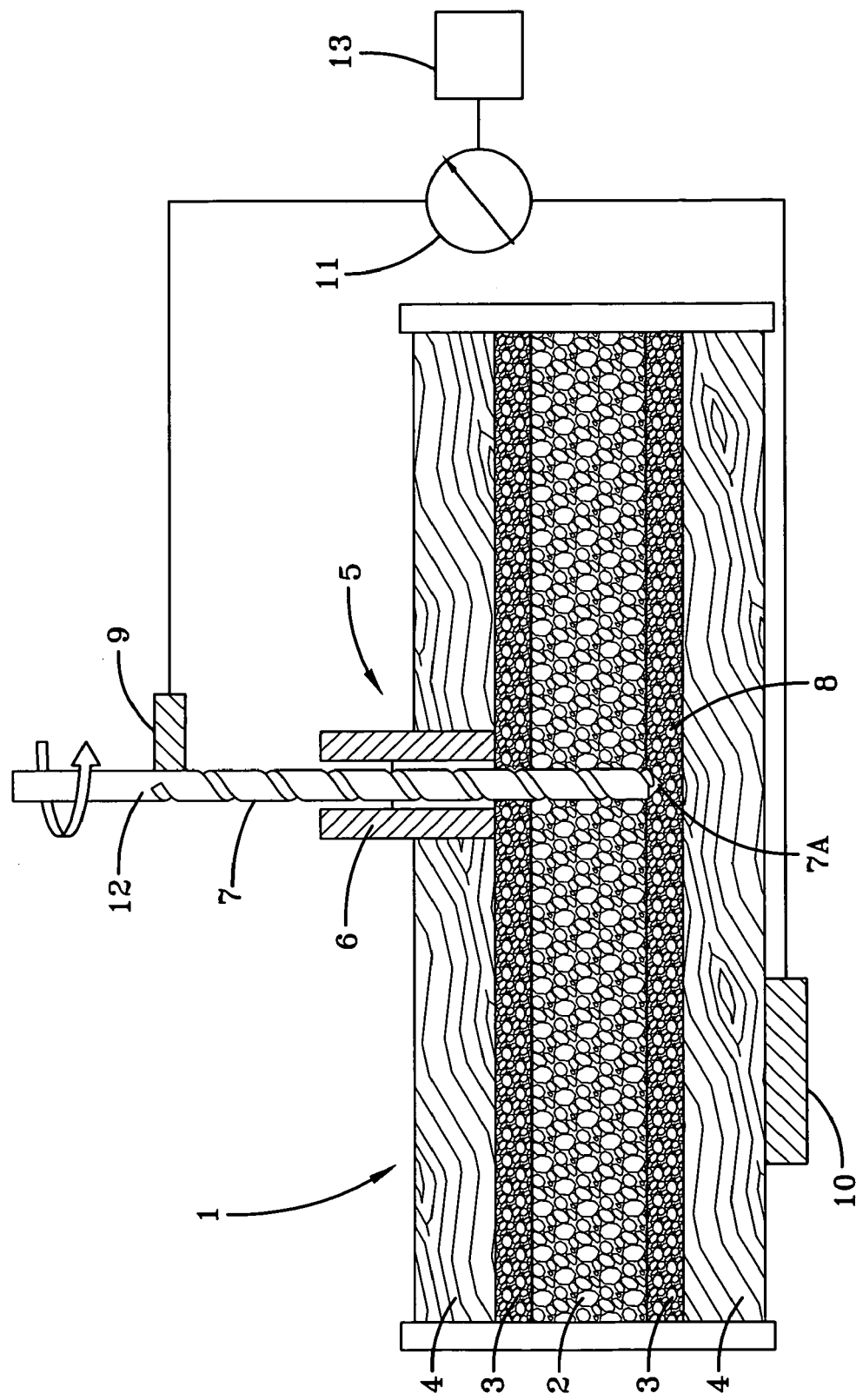
FIG. 1 Schematic drawing to explain a first possible design of the invention related drilling device and the respective drilling procedure.

FIG. 1 schematically shows the principal construction of the invention-related drilling device during a drilling procedure through live bone. The bone (1) in shape of a tube like bone is drawn in cross section. The centre is filled with spongious bone 2 (spongiosa) being surrounded from a cylinder of cortical bone 3 (cortex). The more solid cortex is covered by soft tissue 4, such as muscles, vessels etc.

The soft tissue 4 has been removed at the entry point of the drill 5, exposing cortical bone. At this point a protective socket 6 is used, firstly to prevent the drill from contacting soft tissue, secondly to avoid skidding from the curved surface, thirdly to help guiding the drill 7 in the right direction through the bone. The socket is gently sheeting the drill, allowing enough freedom for unhindered rotation.

As shown in FIG. 1 the tip 7a of the drill 7 has first penetrated the cortex and afterwards the softer spongious bone 2 to settle again in cortical bone 3. For reasons of better definition this part of cortical bone is called opposite cortex 8. At the end of the procedure, the drill will have penetrated the opposite cortex and have reached adjacent soft tissue. At this time it's the skill of the surgeon to stop drilling, before soft tissue is going to be injured.

The invention-related drilling device holds a drill 7, that is being contacted by a bore electrode 9. Vis-à-vis to the drill 7 or to its tip 7a a backing electrode 10 is mounted preferably at an easily accessible site (i.e. patient's skin).

The bore electrode 9 and the backing electrode 10 are connected to a resistance measuring device 11, that is exposing a continuous or alternating current/voltage to the electrodes 9, 10, and thus measuring electrical resistance The drill 7 is a conventional drill made of electrically conducting steel. Except for the tip 7a, however, and an annular surface around the proximal drill shaft in 12 cm distance from the tip, the drill's surface is electrically insulated, i.e. by galvanisation or eloxation.

The bore electrode 9 is getting into contact with the electrically conducting annular surface of the proximal drill 12. Thereby the continuous or alternating voltage of the bore electrode 9 is transmitted to the annular surface 12 and therefore conducted directly to the tip of the drill 7a.

In principal, with this method measuring of the resistance against continuous current of the tissue between the tip of the drill 7a and the backing electrode 10 will be possible. Preliminary experiments however led to the conclusion, that applying alternating voltage and measuring impedance will yield particularly precise data.

Measuring of impedance happens with as low as possible voltages, i.e. 1 volt. The alternating voltage is generated by the resistance-measuring device, subsequently impedance is calculated from the measured current. For this purpose the so-called lock-in-technique seems very suitable. This technique is widely known, which is why further description seems unnecessary. The frequency of the alternating voltage typically ranges between 1 kHz and 100 kHz. Thereby, erratic currents caused by the 50 Hz buzzing or by high frequent couplings can be avoided. Subsequently, the current is only registered within the given range of frequencies (lock-in). Currents of other frequencies are being disregarded. In addition to the amplitude of impedance, its face is determined, too. With the aid of suitable band pass filters, the measured signal is being processed.

As it is of major importance for the surgeon—as explained above—to know about the time of penetrating the opposite cortex 8, the change of impedance between the various tissue types should lead to suitable measures to detect it. This change of impedance, for example, can be monitored by using suitable filters to differentiate the signals according to their maximum.

The RMD 11 is connected to a monitoring device 13 for evaluating the data measured by the RMD. For this purpose, a computer system is hooked up to the monitoring device. This makes it possible to display the tissue type (cortex 3, spongious bone 2, soft tissue 4) and thus to locate the positions of the tip of the drill at a time. By penetrating the opposite cortex 8 and touching the adjacent soft tissue 4, an optical as well as an acoustic signal can be generated. Furthermore, the monitoring device 13 can be used to indicate the depth of the drilled hole.

Figure 2:
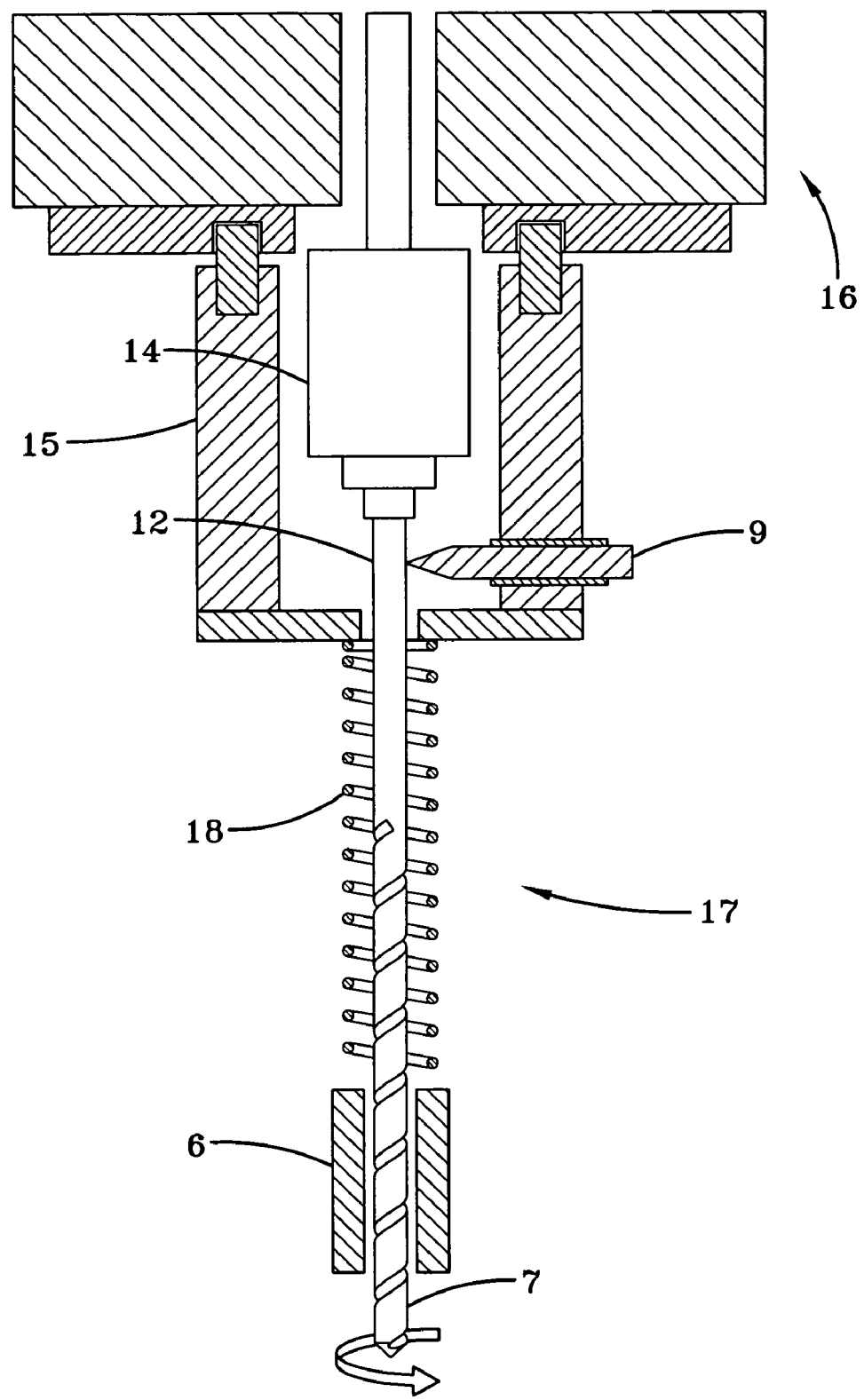
FIG. 2 Schematic drawing of a second possible design of the invention

FIG. 2 shows a second design of the invention related drilling device, while the above-mentioned RMD stays the same.

In detail, according to FIG. 1, FIG. 2 shows, that the drill 7 is hooked up to a drilling chuck 14, which is brought into rotation by a bore drive, which is not particularly illustrated.

The bore electrode 9 contacts a widely known carbon sliding-bow at the annular surface 12 of the drill 7, which is electrically conducting.

For better guiding of the bore electrode 9, it is integrated in a special case. This, in turn, is hooked up, for example by means of a bayonet-clutch, to the main case 16 carrying the drilling device.

In addition to the above described resistance measurement, the second design of the invention also includes the measuring of depth 17 of the drilled hole. The drilling-depth measuring device (DDMD) 17 in FIG. 2 is constructed as follows:

Between the centre piece 16 of the drilling device and the tissue protecting socket 6, a mechanically stretchable and compressible element is mounted, for example a spring 18. This spring can be fixed on one side only, e.g. at the head piece 15 while being loosely attached to the protecting socket 6. By advancing the drill 7, the spring subsequently shortens, while it will extend when the drill is withdrawn. The power necessary to deform the spring can be measured by means of electrical devices for load indication (not drawn in the Fig). Thereby one can measure the degree of advancement of the drill in indicate the distance on the monitor 13 (FIG. 1).

With a signal indicator (not shown here), the surgeon can determine the start-off for measuring the drilling depth. The surgeon can start the signal indicator at the moment he begins drilling. After this onset, the advancement of the drill is continuously measured. Occasional interruption of the drilling procedure does not harm the measurement, because the intercepted computer will calculate only the absolute advancement against the starting point.

In combination with the above-described RMD, the surgeon is continuously being informed about the actual drilling depth, the eventual type of tissue and tissue borders.

Figure 3:
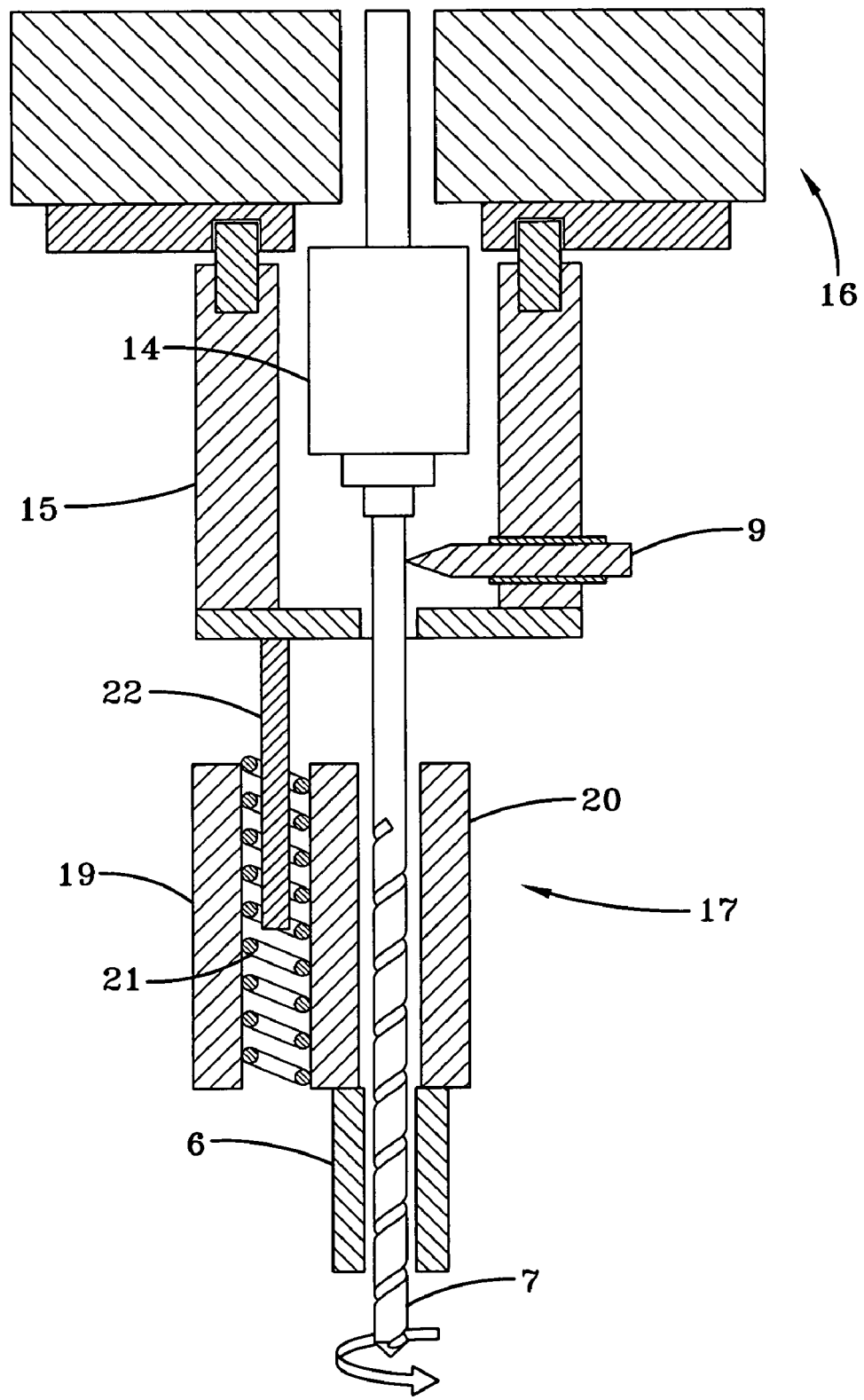
FIG. 3 Schematic drawing of a third design of the invention.

FIG. 3 schematically shows a third design of the invention, which essentially refers to the second design. It only differs in that the DDMD here relies on the principle of magnetic or electromagnetic tools.

For this purpose, the tissue protecting socket 6 is equipped with adding, attachment or support 19, which on the one hand allows the drill to pass on its way through an opening 20, on the other hand carries a magnetic spool 21. This spool 21 is completely encapsulated to ease cleaning and sterilisation. This special adding/attachment support 19 to the socket can also be mounted separately to the case of the drilling device.

In the centre case 16 or the head piece 15 of the drilling device, a ferrite-rod is mounted being also encapsulated for the known reasons. The ferrite-rod 22 intrudes the spool 21 as spool core. Then it is inductivity of the spool from which the advancing of the drill can be calculated and indicated on the monitoring device.

Figure 4:
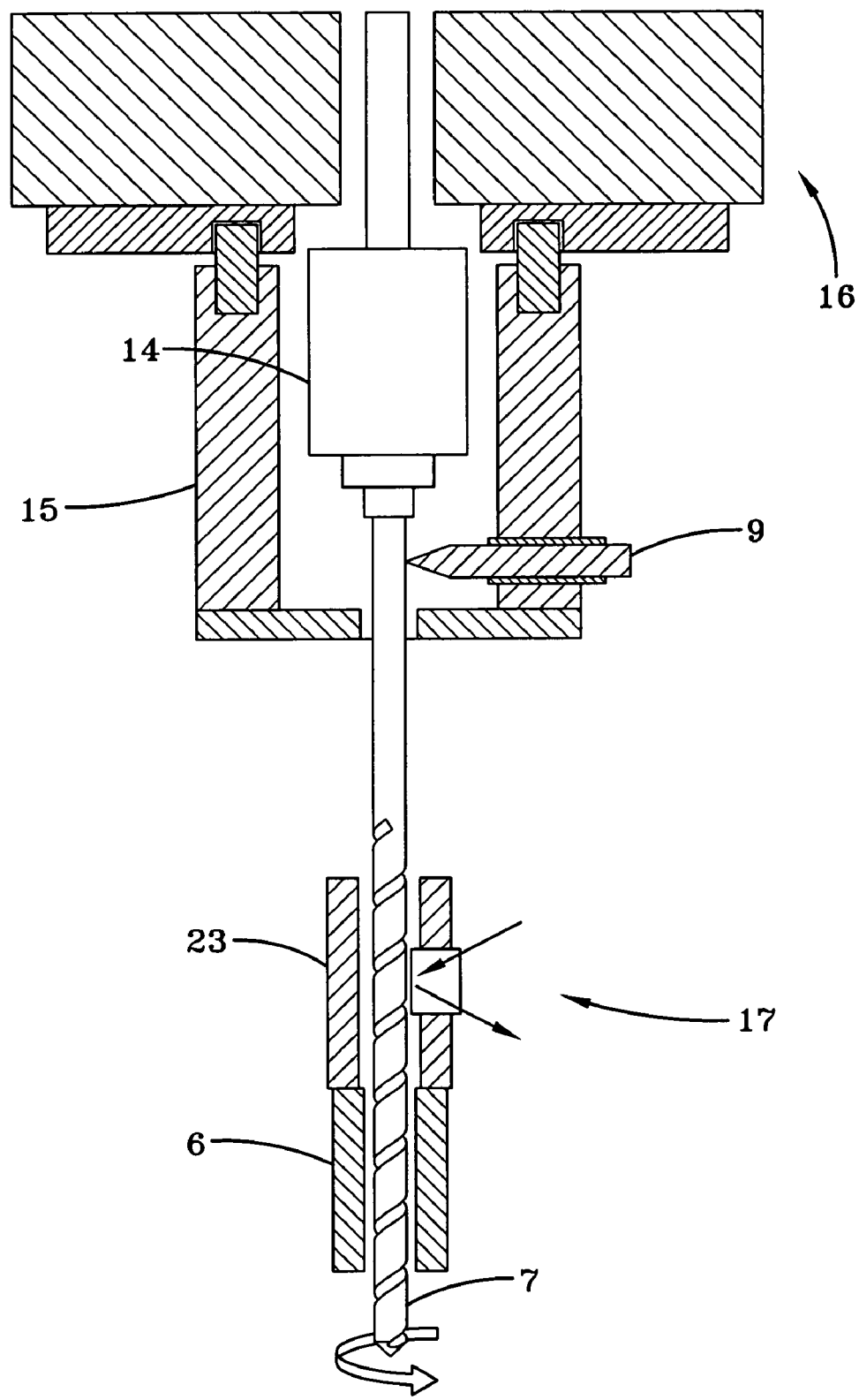
FIG. 4 Schematic drawing of a fourth design of the invention

FIG. 4 finally shows a fourth design of the invention, which differs from the fore-going designs only concerning the DDMD 17. In contrast to the fore-mentioned mechanical and magnetic methods, this design deals with optical measuring.

For this purpose, the drill 7 carries coloured rings, e.g. in a distance of 0.5 mm. The colours can change in the following way: White, Red, Green, White, Red, Green, White.

The tissue protecting socket 6 carries a second measuring socket 23. In this measuring socket 23 two (not illustrated) light sources are focused at the drill (7), where-by the light from the first source, e.g., can be reflected from the green as well as from the white colour ring, whereas the light of the second source can only be reflected from the red and the white colour ring. The reflected light from each source is going to be detected by a photo diode (not illustrated). In a special processing unit (not illustrated) the change in colours detected from the reflections is registered, the sequence is counted and thus direction and degree of bore advancement can be indicated via EDV.

Example: The system can conclude for advancement if the colour changes from white into green, while drawing back the drill is indicated when white changes into red. The resolution of the system amounts to 0.5 mm. A special cleansing device is mounted at the entry of the tissue-protecting socket in order to protect the colour rings from being polluted with blood and bone debris.

The designs as presented in FIGS. 2 and 4 are shown only to explain principle alternatives in the construction of the DDMD. The finally chosen design of this invention has to take into account, that the drilling device can also be used by hand (alternatively by robots), because the surgeon wants to feel the tissue quality. Therefore, the DDMD needs to provide possibilities to determine by hand the drilling speed and the drilling direction and to allow intermediate interruption of the drilling process. This, of course, does not prohibit fixing the DDMD in a special tool, such as a robot.

To improve the precision of measurement, in addition to the change of impedance, the torque of the drilling drive can be measured and used for integrated calculations.

Depending on the tissue borders and the specific tissue resistance, the drill will de- or accelerated. It is known, that deceleration is also due to friction between the cylindrical sidewalls of the drilling hole and the drill itself. It is known, however, that deceleration is predominantly caused by shear load at the tip of the drill. The measurement of torque can be done in different ways: It is possible, to measure the uptake of current by the drive and therefrom draw conclusions on the torque.

The integrated information out of torque of the drill and change of impedance can be evaluated by the processing unit in order to get precise information on the tissue qualities and the location of the tip of the drill at a time. Once the tip of the drill leaves the spongious bone to enter the opposite cortex, not only a change of impedance, but also an increased torque can be measured.

This torque depends on the shear load, which itself depends on the exerted pressure the surgeon is applying. Therefore, it can be useful to additionally measure this pressure by a separate tool.

The information about the exerted drilling pressure helps to calculate a standardised relative torque from the measured absolute torque. This might even more improve the precision of measurement.

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall within the spirit and scope of the appended claims.

The invention claimed is:

1. A medical drilling device for drilling of human or animal bone tissue, said medical drilling device comprising:
   a bore electrode for transmitting electrical current;
   a drill bit having an exterior surface and an interior portion, said drill bit including:
      a drill bit tip for penetrating human or animal bone tissue, the drill bit tip being non-insulated and able to conduct electricity; and
      an annular area on said exterior surface of said drill bit and placeable in electrical contact with said bore electrode, said annular area being non-insulated and able to conduct electricity;

said exterior surface being surface treated with a surface treatment except at said drill bit tip and said annular area, said surface treatment provides electrical insulation such that said exterior surface is unable to conduct electricity except at said drill bit tip and said annular area, said drill bit tip, said annular area and said interior portion of said drill bit being able to conduct electricity;

a bore drive for driving the drill bit, a backing electrode, which is directed in a way, that the tissue to be drilled substantially lies between the backing electrode and the drill bit, a resistance measuring device connected with the bore electrode and with the backing electrode, the two electrodes being exposable to a current for creating an electrical resistance between the drill bit tip and the backing electrode, said bore electrode being in electrical contact with the backing electrode, the resistance between the drill bit tip and the backing electrode being precisely measurable, and a monitoring device operatively connected to said resistance measuring device for indicating information delivered from said resistance measuring device, wherein electrical current is transmittable on said annular area through said interior portion and through said drill bit tip, said resistance measuring device creating the electrical resistance between said drill bit tip and said backing electrode indicative of the type of tissue being drilled and the depth of the drilling, and said monitoring device yielding information about the type of tissue being drilled and a precise measurement of the depth of the drilling, wherein said exterior surface of the drill bit allows electrical contacts only at said drill bit tip and said annular area, said surface treatment provides electrical insulation which prevents errors in resistance measurements and enabling the simultaneous measurement of the type of tissue being drilled and the precise measurement of the depth of the drilling without interruption in the drilling.

2. The medical drilling device according to claim 1, wherein:
the resistance measuring device is an impedance measuring device,
said impedance measuring device is constructed to operatively receive an alternating current, and
the electrical resistance is an electrical impedance.

3. The medical drilling device according to claim 1 wherein the monitoring device is equipped to indicate optical and acoustical signals as a result from data or a change of data against time from the resistance measuring device.

4. The medical drilling device according to claim 1, wherein the monitoring device is equipped with a data processing unit, said data processing unit delivering information about the quality and type of tissue, being hit by the drilling device at a time, the information being based on registration of data or the change of data as measured by the resistance measuring device.

5. The medical drilling device according to claim 4, wherein the data processing unit is provided to control a switch for stopping the bore drive or for providing an optical or acoustical signal when the processing unit detects drilling of a certain tissue type.

6. The medical drilling device according to claim 4, further comprising a torque registration unit for registering torque based on the registration of data or the change of data as measured by the resistance measuring device, wherein the data processing unit delivers a combined evaluation of all data and changes of data measured by the resistance measuring device and the data or changes of data delivered by the torque registration unit such that information becomes available about quality and type of tissue which is penetrated by the drilling device at a respective time.

7. The medical drilling device according to claim 1 and further including a drilling depth measuring device for measuring the advancement of the drilling device according to a defined starting point or a defined set-off position.

8. The medical drilling device according to claim 7, further comprising a signal indicator being connected to the drilling depth measuring device, said signal indicator indicating the start-off time or the position at the beginning of a measuring procedure.

9. The medical drilling device according to claim 7, further comprising a tissue protecting socket for preventing the drilling tool from contacting soft tissue, for preventing skidding of the drilling tool and for guiding the drill.

10. The medical drilling device according to claim 7 wherein the drilling depth measuring device works on the basis of either a mechanical, a spring-mechanical, a magnetic, an electromagnetic, an inductive, a capacity-related or optical measuring principle.

11. The medical drilling device according to claim 1, further comprising a torque measuring device for measuring a specific torque which drives the drilling device during a drilling procedure.

12. The medical drilling device according to claim 11, further comprising:
a manual pressure measuring device for measuring a manual drilling pressure exerted against the tissue by the surgeon during the use of the drilling device, and
a device for calculating a standardized relative torque from a specific torque and the manual drilling pressure.

13. The medical drilling device according to claim 12, further comprising a processing unit for delivering a combined evaluation of all data and changes of data measured by the resistance measuring device and the device for calculating a standardized relative torque from a specific torque such that information becomes available about quality and type of tissue which is penetrated by the drilling device at a respective time.

14. The medical drilling device according to claim 1, wherein said surface treatment comprises galvanization or eloxation (anodization).

15. A method for medical drilling of human or animal tissue comprising the following steps:
providing a drill having a bore electrode;
providing a drill bit having an exterior surface and an interior portion with a non-insulated annular area on the exterior surface and able to conduct electricity, a non-insulated drill bit tip able to conduct electricity for penetrating human or animal bone tissue and the exterior surface being surface treated with a surface treatment except at the drill bit tip and the annular area, where the surface treatment provides electrical insulation such that said exterior surface is unable to conduct electricity except except at the drill bit tip and the annular area the drill bit tip, the annular area and the interior portion of said drill bit being able to conduct electricity;
placing the exterior surface of the drill bit in electrical contact with the bore electrode;
commencing the drilling on one side of the tissue to be drilled;
providing a backing electrode at the side opposite of the one side of the tissue to be drilled;

providing an electrical current from the annular area through the interior portion and through the drill bit tip and into the tissue;

measuring an electrical resistance between the drill bit tip and the backing electrode to obtain a measured data;

registering the measured data or a change against time of the measured data by a processing unit and indicating the measured data to a user.

16. The method according to claim 15, further comprising the step of measuring the electrical resistance of the electrical current through the tissue.

17. The method according to claim 16, further comprising the step of simultaneously measuring penetration of the drill bit through the tissue at the same time of measuring the electrical resistance of the electrical current through the tissue.

18. A medical drilling device for drilling of human or animal bone tissue at a drill site, said medical drilling device comprising:

a bore electrode for transmitting electrical current;
  a drill bit having an exterior surface and an interior portion, said drill bit including:
    a drill bit tip for penetrating human or animal bone tissue, said drill bit tip being non-insulated and able to conduct electricity; and
    an annular area on said exterior surface of said drill bit and placeable in electrical contact with said bore electrode, said annular area being non-insulated and able to conduct electricity;
    said exterior surface being surface treated with a surface treatment except at said drill bit tip and said annular area, said surface treatment provides electrical insulation such that said exterior surface is unable to conduct electricity except at said drill bit tip and said annular drill bit tip and said annular area; said drill bit tip, said annular area and said interior portion of said drill bit being able to conduct electricity;
  a bore drive for driving said drill bit,
  a backing electrode, which is directed in a way, that the tissue to be drilled substantially lies between said backing electrode and said drill bit,
  a resistance measuring device connected with said bore electrode and with said backing electrode, said bore electrode and said backing electrode being exposable to a current for creating an electrical resistance between said drill bit tip and said backing electrode, said bore electrode being in electrical contact with said backing electrode, the resistance between said drill bit tip and said backing electrode being precisely measurable,
  a drilling depth measuring device for measuring the advancement of said drill bit according to a defined starting point or a defined set-off position and indicating a precise measurement of the depth of the drilling; and
  a monitoring device operatively connected to said resistance measuring device and said drilling depth measuring device, said monitoring device indicating information remote from the drill site delivered from said resistance measuring device and said drilling depth measuring device without palpation of the drill site,
  wherein electrical current is transmittable on said annular area through said interior portion and through said drill bit tip, said resistance measuring device creating the electrical resistance between said drill bit tip and said backing electrode indicative of the type of tissue being drilled and the depth of the drilling, and said monitoring device yielding information about the type of tissue being drilled and the precise measurement of the depth of the drilling,
  wherein said exterior surface of the drill bit allows electrical contacts only at said drill bit tip and said annular area, said surface treatment provides electrical insulation which prevents errors in resistance measurements and enabling the simultaneous measurement of the type of tissue being drilled and the precise measurement of the depth of the drilling without interruption in the drilling.

* * * * *